United States Patent
Lee et al.

(10) Patent No.: US 9,339,511 B2
(45) Date of Patent: *May 17, 2016

(54) PHARMACEUTICAL FORMULATION CONTAINING CHOLINE ALFOSCERATE

(71) Applicant: CTC BIO, INC., Seoul (KR)

(72) Inventors: Bong-Sang Lee, Gyeonggi-do (KR); Su-Jun Park, Gyeonggi-do (KR); Do-Woo Kwon, Chungcheongnam-do (KR); Hong-Ryeol Jeon, Gyeonggi-do (KR)

(73) Assignee: CTC Bio, Inc., Seoul (KR)

( * ) Notice: Subject to any disclaimer, the term of this patent is extended or adjusted under 35 U.S.C. 154(b) by 146 days.

This patent is subject to a terminal disclaimer.

(21) Appl. No.: 14/104,062

(22) Filed: Dec. 12, 2013

(65) Prior Publication Data

US 2014/0100192 A1  Apr. 10, 2014

Related U.S. Application Data

(63) Continuation of application No. 12/867,286, filed as application No. PCT/KR2009/000719 on Feb. 13, 2009, now Pat. No. 8,633,176.

(30) Foreign Application Priority Data

Feb. 15, 2008 (KR) .................. 10-2008-0013922

(51) Int. Cl.
*A61K 31/66* (2006.01)
*C07C 261/00* (2006.01)
*A61K 31/685* (2006.01)
*A61K 9/16* (2006.01)

(52) U.S. Cl.
CPC .................. *A61K 31/685* (2013.01); *A61K 9/16* (2013.01); *A61K 9/167* (2013.01); *A61K 9/1611* (2013.01); *A61K 9/1694* (2013.01)

(58) Field of Classification Search
None
See application file for complete search history.

(56) References Cited

U.S. PATENT DOCUMENTS

| 8,633,176 | B2 * | 1/2014 | Lee .......................... | A61K 9/16 514/131 |
|---|---|---|---|---|
| 2003/0171303 | A1 | 9/2003 | Gallop | |
| 2004/0197411 | A1 | 10/2004 | Gao | |
| 2008/0311191 | A1 | 12/2008 | Nangia | |

FOREIGN PATENT DOCUMENTS

EP  1203584 A1  5/2002

OTHER PUBLICATIONS

Stedman's Medical Dictionary, 27th ed., 2000, pp. 380, 1641.

* cited by examiner

*Primary Examiner* — Svetlana M Ivanova
(74) *Attorney, Agent, or Firm* — Yancy IP Law, PLLC

(57) ABSTRACT

The present invention provides choline alfoscerate-containing pharmaceutical preparations which have improved storage-stability and are easily taken. The present invention also provides a method for manufacturing pharmaceutical preparations comprising choline alfoscerate, which is easy and simple and is performed by normal manufacturing equipments.

3 Claims, No Drawings

PHARMACEUTICAL FORMULATION CONTAINING CHOLINE ALFOSCERATE

TECHNICAL FIELD

The present invention relates to choline alfoscerate-containing pharmaceutical preparations and manufacturing methods thereof. The storage-stability and taking-easiness of the pharmaceutical preparations according to the present invention are improved.

BACKGROUND ART

Choline alfoscerate is a medicine used for treating denatured or degenerative organic brain syndrome, and the second symptoms of cerebrovascular diseases. That is, choline alfoscerate is useful for treating senile hypermetamorphosis such as memory impairment, mental derangement, disorientation, and attention deficiency; the change of feeling and behavior such as emotional instability and irritability; senile pseudodepression and so on.

The commercially available preparation of choline alfoscerate is a soft-capsule comprising the liquid phase of choline alfoscerate. In the soft-capsule preparation, choline alfoscerate may move into water-soluble shells made of gelatin over time, and preservatives should be used for preventing microorganism deterioration. Further, because the gelatin capsule is weak to humidity and heat, its disintegration may delay over time. In addition, a specific manufacturing machine is required for the mass-production of soft capsules. In particular, soft capsules are sometimes difficult for aged people whose deglutition movement is weak to swallow.

DISCLOSURE

Technical Problem

Accordingly, the object of the present invention is to provide a choline alfoscerate-containing pharmaceutical preparation which stability and taking-easiness are improved.

Another object of the present invention is to provide a manufacturing method of a choline alfoscerate-containing pharmaceutical preparation which stability and taking-easiness are improved.

Technical Solution

To achieve the object, the present invention provides choline alfoscerate-containing pharmaceutical preparations wherein choline alfoscerate is absorbed into colloidal silicone dioxide. Preferably, in the pharmaceutical preparation of the present invention, the colloidal silicone dioxide is used in an amount of from 0.5 to 1.5 parts by weight per part by weight of choline alfoscerate.

Colloidal silicone dioxide is the most preferable as an absorbent material for the liquid phase of choline alfoscerate, among a lot of pharmaceutical excipients.

In cases of making powder/granule comprising choline alfoscerate, lactose formed granules having too high specific gravity and relatively low surface area, so lactose was not suitable as an absorbent for choline alfoscerate. It also was difficult to control the bad physical characteristics of choline alfoscerate with lactose. Consequently, sticking problems happened when making tablets or filling empty hard capsules, which is thought to be caused by the humidity that could not be controlled by lactose. Big amounts of other excipients will be further required for solving these problems.

In case of using hydroxypropylmethylcellulose as an absorbent, the particle size of granules made of hydroxypropylmethylcellulose and choline alfoscerate was not uniform, and it also was difficult to sieve the granules, even though the specific gravity was somewhat low and its water-absorbing and swelling ability were relatively proper as an absorbent. In addition, preparations made by using hydroxypropylmethylcellulose as an absorbent were difficult to disintegrate, due to the hardness of the tablets or granules after drying.

In case that hydroxypropylcellulose was used as an absorbent for making powder/granule comprising choline alfoscerate, the hardness of granules was too high to disintegrate, and it was also difficult to sieve the granules. In addition, it was difficult to make granules having uniform size.

In case that polyvinylpyrrolidone was used as an absorbent, the size of granules was somewhat uniform and their appearance was also good. Further, there were no problems related to sieving. However, the hygroscopic property of granules was very big, so the storage stability was bad. In addition, there was a problem that the disintegration of preparations (for example, a tablet) was not easy.

In the pharmaceutical preparation of the present invention, the amount of colloidal silicone dioxide for absorbing choline alfoscerate is preferably 0.5 to 1.5 parts by weight per part by weight of choline alfoscerate. If the amount of colloidal silicone dioxide is less than 0.5 part by weight, it is difficult to control the bad physical characteristics of choline alfoscerate and the sticking problem may happen when making tablets or filling hard capsules. If the amount of colloidal silicone dioxide is more than 1.5 parts by weight, a small size of powder may be too much made and the disintegration of the tablet comprising choline alfoscerate may delay.

More preferably, the pharmaceutical preparation of the present invention comprises granules made by both a hydrophilic polymer (preferably, hydroxypropylmethylcellulose and polyvinylpyrrolidone, more preferably, hydroxypropylmethylcellulose) and colloidal silicone dioxide having absorbed choline alfoscerate. This kind of preparation is better than preparations comprising only the mixture (or granules) of choline alfoscerate and colloidal silicone dioxide when considering appearance stability and manufacturing easiness like filling. When further considering the easiness of taking, the preparation is preferably a powder-type or granule-type preparation. More preferably, the viscosity of the hydroxypropylmethylcellulose is 3 to 7 cP when measured at 20□ as a 2% water solution.

Hydroxypropylcellulose, poloxamer, polyox, carrageenan and so on may be used for making granules with the mixture of choline alfoscerate and colloidal silicone dioxide. However, those polymers are less preferable than hydroxypropylmethylcellulose and polyvinylpyrrolidone. In addition, hydroxypropylmethylcellulose is better than polyvinylpyrrolidone in the aspect of stability.

In case that polyvinylpyrrolidone is used for making granules with the mixture of choline alfoscerate and colloidal silicone dioxide, the appearance of granules was not bad, and the viscosity of the granule-making solution was so low that it was possible to make granules with a small amount of solvent. However, the hygroscopic property of granules was relatively big, and the hardness of granules after drying was so big that the disintegration of granules and tablets made of those granules might delay.

In case that hydroxypropylcellulose is used for making granules with the mixture of choline alfoscerate and colloidal silicone dioxide, the viscosity was so high that a large amount of solvent was required to make granules, which consequently caused much more processing time. In addition, the hardness of granules was so big that the disintegration of granules and tablets made of those granules was not easy.

In case that poloxamer is used for making granules with the mixture of choline alfoscerate and colloidal silicone dioxide, the characteristics of granule-making solution and the appearance of granules were not bad, but the large amount of poloxamer was required for blocking choline alfoscerate from oozing outside the granules.

Granules made with polyox were unstable to heat and had the hygroscopic property, so that the storage stability was not good. The size of granules made with carrageenan was not uniform, and the disintegration of the granules was delayed.

The pharmaceutical preparation of the present invention may further comprise fillers, disintegrators, diluents, flavors, sweeteners, lubricants and so on, except for choline alfoscerate, colloidal silicone dioxide for absorbing the liquid phase of choline alfoscerate, and the hydrophilic polymer for making granules.

Preferably, the pharmaceutical preparation of the present invention is a powder-type or granule-type preparation. However, tablets made from the granules according to the present invention and hard-capsules filled with the granules according to the present invention are included in the scope of the present invention.

The present invention also provides a method for manufacturing a choline alfoscerate-containing pharmaceutical preparation, comprising (S1) mixing 0.5 to 1.5 parts by weight of colloidal silicone dioxide with 1 part by weight of choline alfoscerate for colloidal silicone dioxide to absorb choline alfoscerate; and (S2) making granules with both hydroxypropylmethylcellulose and colloidal silicone dioxide having absorbed choline alfoscerate.

Advantageous Effects

As said above, the present invention provides choline alfoscerate-containing pharmaceutical preparations which have improved storage-stability and are easily taken, and manufacturing methods thereof. Specific equipments for making soft-capsule preparations are not required for manufacturing the preparations of the present invention.

MODES FOR CARRYING OUT THE INVENTION

Hereinafter, the present invention is described in considerable detail to help those skilled in the art understand the present invention. However, the following examples are offered by way of illustration and are not intended to limit the scope of the invention. It is apparent that various changes may be made without departing from the spirit and scope of the invention or sacrificing all of its material advantages.

Example 1

Selection of Absorbent Material

As shown in table 1 below, pharmaceutical preparations comprising choline alfoscerate were manufactured to evaluate the various effects of absorbent materials.

TABLE 1

| No. | Ingredient (mg) | Example 1-1 | 1-2 | 1-3 | 1-4 | 1-5 |
|---|---|---|---|---|---|---|
| a | Choline alfoscerate | 200 | 200 | 200 | 200 | 200 |
| b | Colloidal silicon dioxide | 200 | 100 | 100 | 100 | 100 |
|   | Lactose | — | 100 | — | — | — |
|   | Hydroxypropyl-methylcellulose | — | — | 100 | — | — |
|   | Hydroxypropylcellulose | — | — | — | 100 | — |
|   | Polyvinylpyrrolidone | — | — | — | — | 100 |
| c | Hydroxypropyl-methylcellulose | 120 | 120 | 120 | 120 | 120 |
| d | Microcrystalline cellulose | 93.5 | 93.5 | 93.5 | 93.5 | 93.5 |
| e | Crospovidone | 18 | 18 | 18 | 18 | 18 |
| f | Polyethyleneglycol6000 | 12 | 12 | 12 | 12 | 12 |
| g | Magnesium stearate | 6.5 | 6.5 | 6.5 | 6.5 | 6.5 |
| h | Water | q.s. | q.s. | q.s. | q.s. | q.s. |
| i | Ethanol | q.s. | q.s. | q.s. | q.s. | q.s. |

More in detail, tablets comprising choline alfoscerate were manufactured and evaluated by the two methods described below.

Firstly, ingredients a, b and i were mixed, sieved and used as seeds in the following process. Ingredients c, f and h were mixed to make a coating solution, and then the coating solution was sprayed to coat the seeds fluidized in the bed of the fluidized-bed granulator. The made granules were simultaneously dried in the bed. The granules then were sieved and mixed with ingredients d, e and g. The final mixture was compressed to make tablets.

Tablets comprising choline alfoscerate were prepared by another method described below. Ingredients a, b and i were mixed and sieved. Ingredients c, f and h were mixed to make a binding solution. The mixture comprising choline alfoscerate and the binding solution were mixed in a mixer. Granules were made with the mixture, and then sieved and dried. Dried granules were then mixed with ingredients d, e and g. The final mixture was compressed to make tablets.

The manufacturing experiments showed the results as follows: In example 1-1, the inclusion complex had a good appearance, and the mixing and tableting processes were easy. In example 1-2, the mixing and tableting were good, but the inclusion complex was damp, and the granules were not uniform. In example 1-3, the bad characteristics of choline alfoscerate was removed by the absorbing process, but many lumps were made instead of uniform granules, and the lumps were difficult to sieve. In example 1-4, the bad characteristics of choline alfoscerate was not completely removed by the absorbing process, and the viscosity of the coating solution or the binding solution was so high that granules were very hard and not uniform. In example 1-5, the bad characteristics of choline alfoscerate was not removed by the absorbing process. These results are thought to show that colloidal silicone dioxide is the most useful absorbent for absorbing choline alfoscerate.

The disintegration time of tablets made in examples 1-1 to 1-5 was evaluated according to the Method for Evaluating Disintegration Time of the Korea Pharmacopoeia. The results are shown in tablet 2 below.

TABLE 2

| Example | Disintegration Time (min) |
|---|---|
| 1-1 | 9 |
| 1-2 | 13 |
| 1-3 | 15 |

TABLE 2-continued

| Example | Disintegration Time (min) |
|---|---|
| 1-4 | 23 |
| 1-5 | 21 |

As shown in table 2, the disintegration time of example 1-1 was within 10 minutes and the shortest. The total weight of tablets of the examples was 650 mg, which is so big that the contents of other excipients except for the active agent should be reduced to decrease the size. In this case, the contents of disintegrators and diluents will decrease, which will cause the delay of the disintegration time in the end. From this view, the low-specific gravity colloidal silicone dioxide is more useful as absorbent for choline alfoscerate than other absorbents.

Example 2

Weight Ratio of the Absorbent and the Active Agent

As shown in table 3 below, granules comprising choline alfoscerate were prepared to evaluate the various effects of the weight ratio of the absorbent and the active agent, choline alfoscerate.

TABLE 3

| No | Ingredient (mg) | 2-1 | 2-2 | 2-3 | 2-4 | 2-5 |
|---|---|---|---|---|---|---|
| a | Choline alfoscerate | 400 | 400 | 400 | 400 | 400 |
| b | Colloidal silicon dioxide | 800 | 600 | 500 | 300 | 200 |
| c | Hydroxypropylmethylcellulose | 40 | 95 | 150 | 250 | 350 |
| d | Lactose | 50 | — | — | — | — |
| e | Mannitol | 80 | 75 | 85 | 125 | 115 |
| f | Aspartame | 15 | 15 | 15 | 15 | 15 |
| g | Polyethyleneglycol6000 | 5 | 10 | 15 | 25 | 35 |
| h | Sugar | 775 | 770 | 800 | 850 | 850 |
| i | Citric acid | 20 | 20 | 20 | 20 | 20 |
| j | Flavor | 15 | 15 | 15 | 15 | 15 |
| k | Water | q.s. | q.s. | q.s. | q.s. | q.s. |
| l | Ethanol | q.s. | q.s. | q.s. | q.s. | q.s. |
|  | Total | 2,200 | 2,000 | 2,000 | 2,000 | 2,000 |

Granules comprising choline alfoscerate were prepared by a fluidized-bed granulator or a normal granulator as follows:

In case of using the fluidized-bed granulator, the granules were prepared as follows: Ingredients a, b and l were mixed and sieved, and then used as seeds in the following process. Ingredients c, (d,) g and k were mixed to making a coating solution. The coating solution was sprayed to coat the seeds fluidized in the bed of the fluidized-bed granulator. The made granules were simultaneously dried in the bed. The granules were sieved and mixed with ingredients e, f, h, i and j to make the final product.

The normal mixing method was used as follows: Ingredients a, b and l were mixed and sieved. Ingredients c, (d,) g and k were mixed to make a binding solution. The binding solution and the mixture were mixed in a mixer. Made granules were sieved and dried, and then mixed with ingredients e, f, h, i and j to make the final product comprising choline alfoscerate.

The easiness of the manufacturing process and granules were evaluated. In examples 2-1 and 2-2 wherein the content of colloidal silicone dioxide was 150% or more of the active agent, the appearance of the inclusion complex was good, but the higher the content of colloidal silicone dioxide was, the more small size of powder was instead of uniform granules. This is thought to be caused by the weak binding force among the inclusion complexes. This resulted in the large surface of granules, which was difficult to coat. This consequently required more amount of polymer (hydroxypropylmethylcellulose in case of example 2) in the following granulation process. In addition, the yield of examples 2-1 and 2-2 was also low. As a result, the possibility for choline alfoscerate to ooze from granules increased, and the size was too small to be sold as a granule-type formulation. In example 2-5 wherein the content of the absorbent, colloidal silicone dioxide was 50% of the active agent, the formation of small size of powder decreased, but it was difficult to completely remove the bad characteristics of the liquid active agent. Example 2-4 was the most preferable when considering the manufacturing process, the appearance of the inclusion complex, the amount of small size of powder formed in the process, stability and so on.

Example 3

Evaluation of Polymer to Make Granules

As shown in table 4 below, granules comprising choline alfoscerate were prepared to evaluate the various effects of polymers used for making granules.

TABLE 4

| No. | Ingredient (mg) | 3-1 | 3-2 | 3-3 | 3-4 | 3-5 | 3-6 |
|---|---|---|---|---|---|---|---|
| a | Choline alfoscerate | 400 | 400 | 400 | 400 | 400 | 400 |
| b | Colloidal silicon dioxide | 300 | 300 | 300 | 300 | 300 | 300 |
| c | Polyvinylpyrrolidone | 250 | — | — | — | — | — |
|  | Hydroxypropylcellulose | — | 250 | — | — | — | — |

TABLE 4-continued

| No. | Ingredient (mg) | Example 3-1 | 3-2 | 3-3 | 3-4 | 3-5 | 3-6 |
|---|---|---|---|---|---|---|---|
|   | Poloxamer | — | — | 250 | — | — | — |
|   | Polyox | — | — | — | 250 | — | — |
|   | Carrageenan | — | — | — | — | 250 | — |
|   | Hydroxypropylmethylcellulose (5 cp) | — | — | — | — | — | 250 |
| d | Mannitol | 125 | 125 | 125 | 125 | 125 | 125 |
| e | Aspartame | 15 | 15 | 15 | 15 | 15 | 15 |
| f | Polyethyleneglycol6000 | 25 | 25 | 25 | 25 | 25 | 25 |
| g | Sugar | 850 | 850 | 850 | 850 | 850 | 850 |
| h | Citric acid | 20 | 20 | 20 | 20 | 20 | 20 |
| i | Flavor | 15 | 15 | 15 | 15 | 15 | 15 |
| j | Water | q.s. | q.s. | q.s. | q.s. | q.s. | q.s. |
| k | Ethanol | q.s. | q.s. | q.s. | q.s. | q.s. | q.s. |
|   | Total | 2,000 | 2,000 | 2,000 | 2,000 | 2,000 | 2,000 |

The granules of example 3 were prepared and evaluated according to the same two methods by which the granules of example 2 were made. That is, the method using the fluidized-bed granulator and the method using the general mixer were used.

In example 3-1, the viscosity of the binding/coating solution was low, the dissolution of ingredients into the granulation solvent (water) was fast, and the process of spraying and mixing was good. However, the hygroscopic property was so high that there was a possibility that the liquid active agent, choline alfoscerate oozes from the granules. In example 3-2, the viscosity of the binding/coating solution was relatively high, and the required amount of the granulation solvent was so great that the processing time was too long. The drying condition was not good and the drying time was long. In example 3-3, the viscosity of the binding/coating solution was low, the dissolution of ingredients into the granulation solvent (water) was fast, and the process of spraying and mixing was good. However, the coating efficiency was so low that there was a possibility that the liquid active agent oozes from the granules. In example 3-4, the viscosity of the binding/coating solution was low, the dissolution of ingredients into the granulation solvent (water) was fast, the process of spraying and mixing was good, and the flexibility of the polymer was so great that no plasticizer are required for coating. However, the stability of the polymer itself was not good, so that the chain of the polymer was destroyed. In example 3-5, the viscosity of the binding/coating solution was relatively high, and the drying condition was not good and the drying time was long. Consequently, the preparation of example 3-6 was the most preferable when considering the easiness of manufacturing process, the storage stability and so on.

Example 4

Evaluation on the Easiness of Taking

The easiness of taking was evaluated with both the commercially available soft-capsule preparation of choline alfoscerate and the granule (example 2-4) of the present invention. Each unit comprising the same amount of choline alfoscerate was taken once, and the easiness of taking was evaluated with a questionnaire. The results of the soft-capsule were shown in table 5 below, and the results of the granules according to the present invention were shown in table 6 below. Group 1 was composed of 20 persons whose ages were 20~29. Group 2 was composed of 20 persons whose ages were 40~49. Group 3 was composed of 20 persons whose ages were 60~69.

TABLE 5

|   |   | Very Good (5) | Good (4) | Normal (3) | Not Good (2) | Very Bad (1) | Total Score |
|---|---|---|---|---|---|---|---|
| Group 1 | Number | 3 | 4 | 8 | 4 | 1 | 64 |
|         | Score  | 15 | 16 | 24 | 8 | 1 |    |
| Group 2 | Number | 1 | 2 | 5 | 7 | 3 | 45 |
|         | Score  | 5 | 8 | 15 | 14 | 3 |   |
| Group 3 | Number | 0 | 2 | 4 | 9 | 5 | 43 |
|         | Score  | 0 | 8 | 12 | 18 | 5 |   |
|   | Total |   |   |   |   |   | 152 |

TABLE 6

|   |   | Very Good (5) | Good (4) | Normal (3) | Not Good (2) | Very Bad (1) | Total Score |
|---|---|---|---|---|---|---|---|
| Group 1 | Number | 4 | 5 | 6 | 3 | 2 | 66 |
|         | Score  | 20 | 20 | 18 | 6 | 2 |    |
| Group 2 | Number | 5 | 7 | 6 | 2 | 0 | 75 |
|         | Score  | 25 | 28 | 18 | 4 | 0 |    |
| Group 3 | Number | 9 | 8 | 3 | 0 | 0 | 86 |
|         | Score  | 45 | 32 | 9 | 0 | 0 |    |
|   | Total |   |   |   |   |   | 227 |

As shown in tables 5 and 6 above, the total score of the granule according to the present invention was 227, which was higher than the score 152 of the soft capsule by about 50%. In particular, whereas the group 1 in their twenties showed similar results between two preparations, the aged group 3 showed about 50% difference. Therefore, this results show that the granule-type preparation comprising the solidified active agent are better than the commercially available soft-capsule.

Example 5

Stability Evaluation

The stability of the commercially available soft-capsule comprising choline alfoscerate and the granule (example 2-4) of the present invention was evaluated by storing each preparation in conditions of the long storage condition (25° C., 60% RH) and the accelerated condition (40° C., 75% RH). The stability was evaluated from the changes of appearance and content.

More in detail, the appearance change was evaluated as follows: The soft-capsule and example 2-4 were put in HDPE bottles, and the change of the appearance over time was observed at 4, 8, 12, 16, 20, and 24 weeks. The change of content was measured from samples taken out at the times when the appearance was observed. The results of the soft-capsule were shown in table 7 below, and the results of the example 2-4 according to the present invention were shown in table 8 below.

TABLE 7

| | Appearance | | Content (%) | | | |
|---|---|---|---|---|---|---|
| | Long Storage | Accelerated | Long Storage Condition | | Accelerated Condition | |
| Term | Condition | Condition | Inside | Shell | Inside | Shell |
| Initial | Good | Good | 101.3 | — | 101.3 | — |
| 4 wks | Good | Contorted appearance, Hard adherence to one another | 100.4 | — | 94.4 | 3.9 |
| 8 wks | Good | The same as above | 101.1 | — | 85.6 | 12.7 |
| 12 wks | Good | The same as above | 100.0 | — | 66.7 | 28.1 |
| 16 wks | Good | The same as above | 99.5 | — | 65.2 | 28.2 |
| 20 wks | Good | The same as above | 99.0 | 0.8 | 64.1 | 27.8 |
| 24 wks | Firmly hardened gelatin | The same as above | 98.6 | 1.1 | 65.0 | 28.6 |

TABLE 8

| | Appearance | | Content (%) | |
|---|---|---|---|---|
| Term | Long Storage Condition | Accelerated Condition | Long Storage Condition | Accelerated Condition |
| Initial | Good | Good | 101.3 | 101.3 |
| 4 wks | Good | Good | 101.0 | 101.4 |
| 8 wks | Good | Good | 100.9 | 101.4 |
| 12 wks | Good | Good | 101.8 | 102.6 |
| 16 wks | Good | A little aggregated sugar | 99.5 | 99.8 |
| 20 wks | Good | The same as above | 101.4 | 100.4 |
| 24 wks | Good | The same as above | 100.1 | 100.7 |

As shown in tables 7 and 8 above, the example 2-4 showed a good appearance until 24 weeks in the long storage condition, but the soft-capsule showed the firmly hardened gelatin shell at 24 weeks. In the accelerated condition, the granule, the example 2-4 showed a good appearance until 12 weeks, but the soft-capsule showed a severe change of appearance from 4 weeks.

In the evaluation on the content stability, the example 2-4 showed a good stability until 24 weeks in the long storage condition, but the active agent of the soft capsule started to ooze into shells after 20 weeks. In the accelerated condition, the granule, the example 2-4 showed a good stability until 20 weeks, but the active agent of the soft capsule started to ooze into shells from 4 weeks, and about 28% of the active agent oozed into shells at 12 weeks. That is, the ooze of choline alfoscerate in the soft capsule was severe.

What is claimed is:

1. A method for manufacturing a pharmaceutical preparation comprising choline alfoscerate, wherein the method comprises
    (S1) absorbing 1 part by weight of choline alfoscerate into 0.5 to 1.5 parts by weight of colloidal silicone dioxide; and
    (S2) making granules of the colloidal silicone dioxide having absorbed choline alfoscerate with a hydrophilic polymer.

2. The method of claim 1, wherein the hydrophilic polymer is polyvinylpyrrolidone, hydroxypropylmethylcellulose or their mixture.

3. The method of claim 1, wherein the hydrophilic polymer is hydroxypropylmethylcellulose.

* * * * *